United States Patent
Kacian et al.

Patent Number: 5,998,195
Date of Patent: Dec. 7, 1999

[54] HIGHLY-PURIFIED RECOMBINANT REVERSE TRANSCRIPTASE

[75] Inventors: Daniel Louis Kacian; Michael Garth Riggs; James Garfield Putnam, all of San Diego, Calif.

[73] Assignee: Gen-Probe Incorporated, San Diego, Calif.

[21] Appl. No.: 08/821,948

[22] Filed: Mar. 21, 1997

Related U.S. Application Data

[63] Continuation of application No. 08/443,781, May 18, 1995, abandoned, which is a continuation of application No. 08/221,804, Apr. 1, 1994, abandoned.

[51] Int. Cl.[6] ............... C12N 1/20; C12N 9/12; C07H 21/04
[52] U.S. Cl. ............... 435/252.33; 435/252.3; 435/194; 536/23.2
[58] Field of Search ............... 435/194, 252.3, 435/419, 325, 252.33; 536/23.2, 24.1, 24.2

[56] References Cited

U.S. PATENT DOCUMENTS

| | | | |
|---|---|---|---|
| 4,943,531 | 7/1990 | Goff et al. | 435/194 |
| 5,017,492 | 5/1991 | Kotewicz et al. | 435/252.3 |

OTHER PUBLICATIONS

Kelly et al., RNase PH is Essential for tRNA Processing and Viability in RNase–deficient *Escherichia coli* Cells. *J. Biol. Chem.* 267(23):16015–16018 (1992).

Durwald, H. and H. Hoffman–Berling, Endonuclease I–deficient and ribonuclease I–deficient *Escherichia coli* mutants. *J. Mol. Biol.* 34:331–346 (1968).

Hautala, et al., Increased expression of a euraryotic gene in *Eschcrichia coli* through stabalization of its messenger RNA. *Proc. Natl. Acad. Sci. USA* 76(11):5774–5778 (1979).

Hu, et al., Murine Leukemia virus pol gene products: analysis with antisera generated against reverse transcriptase and endonuclease fusion proteins expressed in *Escherichia coli*. *J. Virol.* 60(1):267–271 (1986).

Kotewicz, et al., Cloning and overexpression of Moloney murine Leukemia virus reverse transriptase in *Escherichia coli*. 35:249–258 (1985).

Hizi, A. and S. Hughes, Expression in *Escherichia coli* a Moloney murine Leukemia virus reverse transcriptase whose structure closely resembles the viral enzyme. *Gene* 66:319–323 (1988).

Telesnitsky, A. and S. Goff, RNase H domain mutations affect the interaction between Moloney murine leukemia virus recerse transcriptase and its primer template. *Proc. Natl. Acad. Sci. USA* 90:1276–1280 (1993).

Amann, E. et al., Gene, vol. 69, pp. 301–315, 1988.

Durwald, H. et al., J. Mol. Biol., vol. 34, pp. 331–346, 1968.

*Primary Examiner*—Ponnathapu Achutamurthy
*Assistant Examiner*—Peter P. Tung
*Attorney, Agent, or Firm*—Christine A. Gritzmacher; Carlos A. Fisher

[57] ABSTRACT

A plasmid for expression of Moloney Murine Leukemia Virus-derived reverse transcriptase in *E. coli* cells deficient in the expression of indigenous RNAse activity, a method for purification of the recombinant enzyme, and a composition comprising a cloned and purified reverse transcriptase opimized for use in cDNA and nucleic acid amplification procedures.

22 Claims, 12 Drawing Sheets pUC 18      AGGAAACAGCTATG.ACC.ATG.ATT.ACG.AAT.TC pUC 18N     AGGAAACAGCCATG.GCC.ATG.ATT.ACG.AAT.TC
                         Nco I                    Eco R I
         ribosome
         binding
           site Pvu II site
Oligo #1   5'-   GGCATGCCAGCTGGCACGACAGGTTCCCGACTGGAAA
Oligo #1         GCGGGCAGTGAGCGCAACGCAATTAATGTGAGTAGCT
Oligo #1         CACTCATTAGGCACCCCCAGGCTTTACACTTTATGCTTCC  -3'
Oligo #2   3'-   CCGTGGGGTCCGAAATGTGAAATACGAAGG
Oligo #2         CCGAGCATACAACACACCTTAACACTCGCCTATTTGAAA
Oligo #2         GTGTGTCCTTGTCGGTACTAATGCTTAAGCTCGAA  -5'
                                                    Eco RI site

FIG. 2

| | | Distance from RBS to ATG |
|---|---|---|
| E. coli 16S rRNA 3'-5' | (3' end) ATT CCTCCACTAGGT T...... | |
| pUC lacZ | CACACAGGAAACAGCT ATG | 7 |
| pUC18N lacZ | CACACAGGAAACAGCC ATG G | 7 |
| Jespers et al "R" gene (natural) | AAAGCCGGAGTAGAAG ATG | 6 |
| Jespers et al "R" gene (improved) | ATATAAGGAGGTTAAAAT ATG | 7 |
| Jay et al synthetic (Improved) | GCATAAGGAGGTTAAGCT (4-5 bases) | (11-12) |
| SD7 | CACTAAGGAGGTTAAACC ATG G | 7 |
| SD8 | CACTAAGGAGGTTAA g/t ACC ATG G | 8 |
| SD9 | CACTAAGGAGGTTAA g/t/a/t ACC ATG G | 9 |

FIG. 3

| | | |
|---|---|---|
| Oligo #5 | 5'- GAGCTCGAATTCGTAATCATGGCCATGG | TTAAACCTCCTTAGTG |
| Oligo #6 | GAGCTCGAATTCGTAATCATGGCCATGGT at | TTAAACCTCCTTAGTG |
| Oligo #7 | GAGCTCGAATTCGTAATCATGGCCATGGT at at | TTAAACCTCCTTAGTG |
| | | |
| Oligo #5 | AAATTGTTATCCGCTCACAATTCCACACAACATACGAGCCGGAAGCAT | |
| Oligo #6 | AAATTGTTATCCGCTCACAATTCCACACAACATACGAGCCGGAAGCAT | |
| Oligo #7 | AAATTGTTATCCGCTCACAATTCCACACAACATACGAGCCGGAAGCAT | |
| | | |
| Oligo #5 | AAAGTGTAAAGCCTGGGGTGCC -3' | |
| Oligo #6 | AAAGTGTAAAGCCTGGGGTGCC | |
| Oligo #7 | AAAGTGTAAAGCCTGGGGTGCC | |

FIG. 4

Oligomer #8  5'-    AGGCAGCCATCACAGAGACTCCAGACACCTCTACCCTCCTCTAATA    -3'

Oligomer #9  3'- CTTTCCGTCGGTAGTGTCTCTGAGGTCTGTGGAGATGGGAGGAGATTATTCGA -5'

FIG. 7

SEQUENCE LISTING (1) GENERAL INFORMATION:

(iii) NUMBER OF SEQUENCES:   13

(2) INFORMATION FOR SEQ ID NO:   1:

(i) SEQUENCE CHARACTERISTICS:
      (A) LENGTH:            114

```
              (B) TYPE:             nucleic acid
              (C) STRANDEDNESS:     single
              (D) TOPOLOGY:         linear (ii) SEQUENCE DESCRIPTION: SEQ ID NO: 1:

GGCATGCAGC TGGCACGACA GGTTTCCCGA CTGGAAAGCG GCCAGTGAGC         50

GCAACGCAAT TAATGTGAGT TAGCTCACTC ATTAGGCACC CCAGGCTTTA        100

CACTTTATGC TTCC                                               114

(2) INFORMATION FOR SEQ ID NO:   2:

(i) SEQUENCE CHARACTERISTICS:
              (A) LENGTH:           112
              (B) TYPE:             nucleic acid
              (C) STRANDEDNESS:     single
              (D) TOPOLOGY:         linear (ii) SEQUENCE DESCRIPTION: SEQ ID NO: 2:

AAGCTCGAAT TCGTAATCAT GGCCATGGCT GTTTCCTGTG TGAAAGTTTT         50

ATCCGCTCAC AATTCCACAC AACATACGAG CCGGAAGCAT AAAGTGTAAA        100

GCCTGGGGTG CC                                                 112

(2) INFORMATION FOR SEQ ID NO:   3:

(i) SEQUENCE CHARACTERISTICS:
              (A) LENGTH:           24
              (B) TYPE:             nucleic acid
              (C) STRANDEDNESS:     single
              (D) TOPOLOGY:         linear (ii) SEQUENCE DESCRIPTION: SEQ ID NO: 3:

CATGGGTCTG AACATCGAAG ATGA                                     24

(2) INFORMATION FOR SEQ ID NO:   4:

(i) SEQUENCE CHARACTERISTICS:
              (A) LENGTH:           20
              (B) TYPE:             nucleic acid
              (C) STRANDEDNESS:     single
              (D) TOPOLOGY:         linear (ii) SEQUENCE DESCRIPTION: SEQ ID NO: 4:

TCATCTTCGA TGTTCAGACC                                          20

(2) INFORMATION FOR SEQ ID NO:   5:

(i) SEQUENCE CHARACTERISTICS:
              (A) LENGTH:           115
              (B) TYPE:             nucleic acid
              (C) STRANDEDNESS:     single
              (D) TOPOLOGY:         linear (ii) SEQUENCE DESCRIPTION: SEQ ID NO: 5:

GAGCTCGAAT TCGTAATCAT GGCCATGGTT TAAACCTCCT TAGTGAAATT         50

GTTATCCGCT CACAATTCCA CACAACATAC GAGCCGGAAG CATAAAGTGT        100

AAAGCCTGGG GTGCC                                              115

(2) INFORMATION FOR SEQ ID NO:   6:

(i) SEQUENCE CHARACTERISTICS:
              (A) LENGTH:           116
              (B) TYPE:             nucleic acid
              (C) STRANDEDNESS:     single
              (D) TOPOLOGY:         linear
```

(ii) SEQUENCE DESCRIPTION: SEQ ID NO: 6:

| | |
|---|---|
| GAGCTCGAAT TCGTAATCAT GGCCATGGTW TTAAACCTCC TTAGTGAAAT | 50 |
| TGTTATCCGC TCACAATTCC ACACAACATA CGAGCCGGAA GCATAAAGTG | 100 |
| TAAAGCCTGG GGTGCC | 116 |

(2) INFORMATION FOR SEQ ID NO: 7:

(i) SEQUENCE CHARACTERISTICS:
        (A) LENGTH:       117
        (B) TYPE:         nucleic acid
        (C) STRANDEDNESS: single
        (D) TOPOLOGY:     linear (ii) SEQUENCE DESCRIPTION: SEQ ID NO: 7:

| | |
|---|---|
| GAGCTCGAAT TCGTAATCAT GGCCATGGTW WTTAAACCTC CTTAGTGAAA | 50 |
| TTGTTATCCG CTCACAATTC CACACAACAT ACGAGCCGGA AGCATAAAGT | 100 |
| GTAAAGCCTG GGGTGCC | 117 |

(2) INFORMATION FOR SEQ ID NO: 8:

(i) SEQUENCE CHARACTERISTICS:
        (A) LENGTH:       23
        (B) TYPE:         nucleic acid
        (C) STRANDEDNESS: single
        (D) TOPOLOGY:     linear (ii) SEQUENCE DESCRIPTION: SEQ ID NO: 8:

| | |
|---|---|
| TACCTTGTTA CGACTTCACC CCA | 23 |

(2) INFORMATION FOR SEQ ID NO: 9:

(i) SEQUENCE CHARACTERISTICS:
        (A) LENGTH:       16
        (B) TYPE:         nucleic acid
        (C) STRANDEDNESS: single
        (D) TOPOLOGY:     linear (ii) SEQUENCE DESCRIPTION: SEQ ID NO: 9:

| | |
|---|---|
| CTTAGATGCT TTCAGC | 16 |

(2) INFORMATION FOR SEQ ID NO: 10:

(i) SEQUENCE CHARACTERISTICS:
        (A) LENGTH:       46
        (B) TYPE:         nucleic acid
        (C) STRANDEDNESS: single
        (D) TOPOLOGY:     linear (ii) SEQUENCE DESCRIPTION: SEQ ID NO: 10:

| | |
|---|---|
| AGGCAGCCAT CACAGAGACT CCAGACACCT CTACCCTCCT CTAATA | 46 |

(2) INFORMATION FOR SEQ ID NO: 11:

(i) SEQUENCE CHARACTERISTICS:
        (A) LENGTH:       53
        (B) TYPE:         nucleic acid
        (C) STRANDEDNESS: single
        (D) TOPOLOGY:     linear (ii) SEQUENCE DESCRIPTION: SEQ ID NO: 11:

| | |
|---|---|
| AGCTTATTAG AGGAGGGTAG AGGTGTCTGG AGTCTCTGTG ATGGCTGCCT | 50 |
| TTC | 53 |

(2) INFORMATION FOR SEQ ID NO: 12:

(i) SEQUENCE CHARACTERISTICS:
        (A) LENGTH:        15
        (B) TYPE:          nucleic acid
        (C) STRANDEDNESS:  single
        (D) TOPOLOGY:      linear (ii) SEQUENCE DESCRIPTION: SEQ ID NO: 12:

ATGGGTCTGA ACATC                                                          15

(2) INFORMATION FOR SEQ ID NO: 13:

(i) SEQUENCE CHARACTERISTICS:
        (A) LENGTH:        19
        (B) TYPE:          nucleic acid
        (C) STRANDEDNESS:  single
        (D) TOPOLOGY:      linear (ii) SEQUENCE DESCRIPTION: SEQ ID NO: 13:

TAAGGAGGTT TAAAAAACC                                                 19

HIGHLY-PURIFIED RECOMBINANT REVERSE TRANSCRIPTASE

This is a file-wrapper continuation of Ser. No. 08/443,781, filed May 18, 1995, now abandoned, which is a continuation of Ser. No. 08/221,804, filed Apr. 1, 1994, now abandoned, to which this application claims priority.

BACKGROUND OF THE INVENTION

Retroviruses are a group of viruses whose genetic material consists of single-stranded RNA. Following adsorption and entry of the retroviral RNA into the host cell, the viral RNA serves as a template for the synthesis of a complementary DNA strand. The DNA is then made double-stranded through the action of an enzyme having DNA polymerase activity; it is this double-stranded DNA which integrates into the host genome. The RNA-directed DNA polymerase activity responsible for the synthesis of complementary DNA from the viral RNA template is commonly called reverse transcriptase.

Retroviruses are of particular interest because a number of retroviruses have been implicated as the causative agents of various cancers, and other diseases. A retrovirus, human immunodeficiency virus, is the causal agent of acquired immunodeficiency syndrome (AIDS). Additionally, the reverse transcriptase enzymes themselves have become important reagents in molecular biology because of their ability to make complementary DNA from almost any RNA template. Thus, reverse transcriptase is commonly used to make nucleic acids for hybridization probes and to convert single-stranded RNA into a double-stranded DNA for subsequent cloning and expression.

Recently, reverse transcriptases have been used as a component of transcription-based amplification systems. These systems amplify RNA and DNA target sequences up to 1 trillion fold. See e.g., Burg et al., PCT Patent Application WO 89/01050 (1988); Gingeras et al., PCT Patent Application WO 88/10315 (1988); Davey and Malek, European Patent Application EPO 0329822 (1988); Gingeras et al., European Patent Application EPO 0373960 (1989); Malek and Davey, PCT Patent Application WO 91/02814 (1989); Kacian and Fultz, European Patent Application EPO 0408295 A2 (1990). All of these references are hereby incorporated by reference into this disclosure.

Some of the transcription-based amplification methods are exceptionally convenient since the amplification reaction according to these methods is isothermal. Thus, these systems are particularly suited for routine clinical laboratory use in diagnostic tests. Detection of pathogens causing infectious diseases and gene sequences associated with cancers or genetic diseases are among the most important uses of such tests. Reverse transcriptases are also employed as an initial step in some protocols when the polymerase chain reaction (PCR) is used to amplify an RNA target. See Malek et al., U.S. Pat. No. 5,130,238 (1992); and Mocharla et al., Gene 99:271–275 (1990). In such "RT-PCR" procedures, the reverse transcriptase is used to make an initial complementary DNA (cDNA) copy of the RNA target, which is then amplified by successive rounds of DNA replication.

The retroviral reverse transcriptases have three enzymatic activities: a RNA-directed DNA polymerase activity, a DNA-directed DNA polymerase activity, and an RNAse H activity. See Verma, *The Reverse Transcriptase, Biochim. Biophys. Acta* 473:1–38 (1977). The latter activity specifically degrades RNA contained in an RNA:DNA duplex. Degradation of the RNA strand of RNA:DNA intermediates by RNAse H is an important component of some transcription-based amplification systems and is to be distinguished from unwanted degradation due to contaminating nucleases, which interferes with amplification.

A disadvantage of the transcription-based amplification systems is their sensitivity to even trace amounts of nucleases. Since a number of important diseases may yield samples containing very few target nucleic acid molecules, the detection of small amounts of the target is often crucial for an accurate and timely diagnosis. Indeed, the value of target amplification methods is most important when the number of target molecules is low. At low input levels of the target nucleic acids, unwanted degradation of RNA targets or RNA or DNA reaction intermediates can lead to amplification failures and consequent misdiagnosis. Ribonuclease contamination is also a problem in RT-PCR reactions, since loss of the RNA target can lead to amplification failure.

Ribonucleases are relatively ubiquitous, and, in particular, are found in high concentrations in a variety of biological materials, including preparations of retroviruses and in cells commonly used to express recombinant proteins. Ribonucleases frequently contaminate reverse transcriptase preparations from a variety of sources and have been reported to interfere with synthesis of cDNAs, preparation of probes, and other uses besides target amplification alone. Often, an RNase inhibitor is included in the reaction to minimize the deleterious effects of this contamination. See e.g., Maniatis et al., *Molecular Cloning: A Laboratory Manual* 8.11–8.13 (2d ed. Cold Spring Harbor Laboratory Press 1989), hereby incorporated by reference herein.

However, a number of substances commonly used to inhibit or inactivate RNAses, including detergents, chaotropes, organics, metals, proteases and metals are inappropriate for use in target amplification systems since they will inhibit the enzymes used for amplification as well. RNAse-inhibiting proteins such as human placental RNAse inhibitor, Blackburn et al., *J. Biol. Chem.* 252:5904 (1977) or rat liver RNAse inhibitor, Gribnau et al., Arch. Biochem. Biophys. 130:48–52 (1969), may be unstable, are expensive, and can contribute additional interfering substances such as nucleic acids and RNAses that are not inhibited by the inhibitor.

In addition to nucleases, traces of other enzymes, nucleic acids, and certain buffer salts may interfere with amplification reactions. While these substances are merely undesirable for many uses of reverse transcriptase, because of the nature of the amplification reaction it is critical that the enzyme preparation contain as low an amount of them as possible.

Isolation and purification of reverse transcriptase from various sources have been reported. In cases where the enzyme is isolated directly from virus particles, cells, or tissues, the cost is too high for widespread commercial use in diagnostic tests. See e.g., Kacian et al., *Biochim. Biophys. Acta* 46:365–83 (1971); Yang et al., *Biochem. Biophys. Res. Comm.* 47:505–11 (1972); Gerard, et al., *J. Virol.* 15:785–97 (1975); Liu et al., *Arch. Virol.* 55 187–200 (1977); Kato et al., *J. Virol. Methods* 9:325–39 (1984); Luke, et al. *Biochemistry* 29:1764–69 (1990); Le Grice et al., *J. Virol.* 65:7004–07 (1991). Additionally, these methods have not assured removal of substances that are significant inhibitors or contaminants that interfere with the use of reverse transcriptase for target amplification reactions. Another important consideration in the use of reverse transcriptases for a variety of purposes is the RNase H activity associated with the enzyme. The amount of RNase H activity and the way in which the RNase H activities work in coordination with the RNA- and DNA-dependent reverse transcriptase activities are important features affecting the utility of the enzyme for various purposes including transcription-based amplification systems. Too much or too little activity, the wrong kind of activity (such as non-specific RNases), or activities poorly coordinated with DNA synthesis can all lead to reduced performance in a particular application. Proper balance of the synthetic and degradative activities must be maintained; this is not only a function of the particular reverse transcriptase enzyme used, but also is dependent on the ability of the purification protocol to remove the RNA and/or DNA degrading activities.

The cloning and expression of reverse transcriptases in bacterial hosts has been previously reported. Attempts to clone and express reverse transcriptase from avian myeloblastosis virus (AMV-RT) did not lead to production of significant amounts of the purified enzyme. This is apparently due to the fact that the AMV-RT consists of two polypeptide chains, the α and β chains, which must form a dimeric structure and undergo specific post-translational modifications in order to produce fully active enzyme. These same modifications do not occur when the gene is expressed in E. coli.

By contrast to the avian viral RTs, many reverse transcriptases derived from mammalian viruses consist of only one polypeptide chain; efforts to clone and express these enzymes have been more successful. In particular, Goff et al., U.S. Pat. No. 4,943,531 (1990) and Kotewicz et al., U.S. Pat. No. 5,017,492 have described methods for the purification of reverse transcriptase derived from Moloney Murine Leukemia Virus (MMLV-RT) and expressed in E. coli, which methods form the basis for the majority of commercial reverse transcriptase preparations.

Many commercial preparations of reverse transcriptase have been found unsuitable for use in target amplification and for other purposes due to nuclease contamination. See Sambrook, supra, previously incorporated by reference herein; Ryskov et al., Mol. Biol. Rep. 8:213–16 (1982). Other problems with commercial preparations of MMLV-RT may be related to an altered coordination between the DNA synthesis and RNAse H activities of the purified enzyme, reduced ability to bind and initiate synthesis at primer sites or to read through regions of tight secondary structure, or alternately may be due to DNase and other protein contamination. See Agronovsky, A. A., Anal. Biochem. 203:163–65 (1992). Additionally, commercial preparations made using the previously available methods for purification show significant lot-to-lot variability.

Moreover, due in part to the lengthy and labor-intensive purifications employed, the expense of the reagents and equipment employed for scale-up and the low yields of enzyme, the cost of such enzymes is prohibitive for their widespread commercial application in target amplification systems.

It is therefore an object of the present invention to provide an improved form of reverse transcriptase having the correct balance of DNA synthetic activities and RNAse H digestive activities, thereby being particularly suited for use in nucleic acid amplification methods.

It is another object of the present invention to provide a convenient source of reverse transcriptase containing low Levels of contaminants, such as undesired RNAses, that interfere with transcription-based amplification reactions by cloning and expressing a gene coding for an MMLV-RT enzyme having these properties in an E. coli host.

It is yet another object of the present invention to reduce the RNAse activity associated with the enzyme prior to and following purification by cloning and expressing the MMLV-RT gene in a ribonuclease-deficient strain of E. coli.

It is another object of the present invention to develop a simple purification scheme for the isolation of the enzyme.

It is a further object of the present invention to provide methods for the purification of the enzyme that achieve high levels of purity of RT at a low cost.

SUMMARY OF THE INVENTION

The present invention features an expression vector or plasmid containing a cloned version of the gene for MMLV-RT which, when used to transform a suitable host cell such as E. coli, leads to the expression of the gene and the generation of a gene product having the DNA- and RNA-directed DNA polymerase activities and RNAse H activity associated with retroviral reverse transcriptases.

The present invention also features a plasmid containing a gene for MMLV-RT inserted into a host cell which has a reduced level of ribonuclease activity as compared to wild-type strains.

The present invention also includes methods for the purification of the resulting enzyme from the host cells, such methods comprising suitable growth media, fermentation conditions, harvesting and storage of the cells, cell lysis and chromatography.

The present invention also features the enzyme produced by the expression vectors, host cells, and purification procedures of the present invention. The enzyme is highly-purified and suitable for use in nucleic acid amplification and other genetic engineering procedures.

Finally, the present invention features the use of the enzyme produced by the methods described herein for the synthesis of complementary DNA for a variety of purposes, notably in transcription-based amplification and RT-PCR reactions.

BRIEF DESCRIPTION OF THE DRAWINGS

FIG. 2: Oligonucleotides used to construct plasmid pUC18N.

FIG. 3: Alignments of the ribosome binding sites.

FIG. 4: Oligonucleotides used in the construction of improved RBS vectors to modify the ribosome binding site and spacer region.

FIG. 7: Oligonucleotides used to construct the 3' end of plasmid pUC18 MMLV Tailed.

DETAILED DESCRIPTION OF THE INVENTION

Definitions

Figures 1A, 1B:
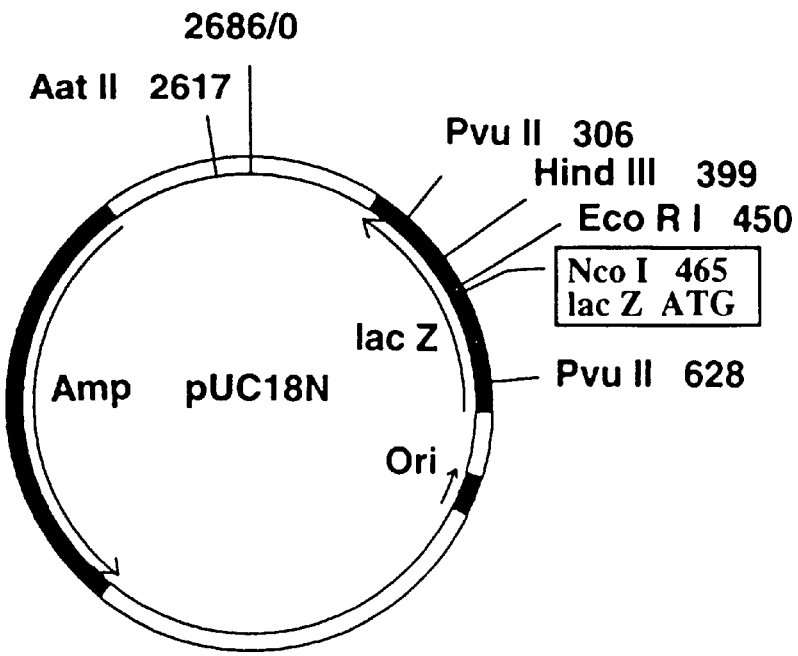
FIG. 1A and 1B: Construction of plasmid pUC18N

As used herein the following terms have the indicated meanings unless expressly indicated otherwise.

By "selectable marker gene" is meant a DNA fragment encoding a gene which, when carried and expressed by a host cell, is capable of conferring a growth advantage to that host cell as compared to cells not containing the selectable marker gene when both are grown in a culture media of a given composition. For example, the gene encoding β-lactamase will confer resistance to amplicillin on host cells containing this gene, whereas cells not containing the gene will be sensitive to ampicillin; thus only cells expressing the gene for β-lactamase will grow in media containing amplicillin. Similarly, cells unable to catabolize an essential amino acid will not grow in media not containing that amino acid, whereas cells containing a gene allowing the cell to make the essential amino acid will grow in the same media.

A selectable marker gene may be covalently linked, for example in a plasmid or expression vector, to one or more other gene or genetic element as a means of identifying cells containing both the selectable gene and the "silent" gene(s) and/or genetic element(s).

By a "purified" nucleic acid or protein is meant a nucleic acid or protein subjected to at least one step which removes cellular components such as carbohydrates, lipids, unwanted nucleic acids, or unwanted proteins from the indicated nucleic acid or protein.

By "upstream" is meant to the 5' side of a given locus on a nucleic acid strand, or in the case of a double stranded nucleic acid molecule, to the 5' side of a particular locus with respect to the direction of gene transcription in that region of the nucleic acid molecule.

By "downstream" is meant to the 3' side of a given locus on a nucleic acid strand, or in the case of a double stranded nucleic acid molecule, to the 3' side of a particular locus with respect to the direction of gene transcription in that region of the nucleic acid molecule.

By "$T_m$" is meant the temperature at which 50% of a population of a double-stranded nucleic acid molecules, or nucleic acid molecules having a double-stranded region, become single-stranded or thermally denatured.

By "recombinant" is meant that a nucleic acid molecule or protein is at least partially the result of in vitro biochemical techniques. A "recombinant DNA molecule" is thus a non-naturally occurring molecule. Such recombinant molecules include, but are not limited to molecules which comprise restriction endonuclease fragments, in vitro nucleic acid ligation products, in vitro exonuclease fragments, and expression vectors comprising heterologous genetic elements such as one or more of the following: promoters, repressor genes, selectable marker genes, temperature-sensitive DNA replication elements, structural genes, and the like.

"Recombinant" proteins or enzymes are those not found in nature. These include purified protein preparations and proteins produced from recombinant DNA molecules. The latter proteins are usually expressed in a heterologous host cell, i.e., one not native to the protein or enzyme in question. However, the gene encoding a recombinant protein may reside on an expression vector contained within a host cell of the same species as the organism from which the protein in question was derived.

By "truncated" is meant a smaller version of the gene or protein in question; with respect to the primary nucleotide or amino acid sequence, a truncated form of a reference nucleic acid or protein is one that lacks one or more nucleotides or amino acids as compared to the reference molecule.

By "substantial sequence homology" is meant that a first nucleic acid or protein molecule has a recognizably non-random similarity to a second reference nucleic acid or protein over at least about 89% of its nucleotide or amino acid sequence respectively.

By a nucleic acid or protein "domain" is meant at least one definite region of contiguous nucleotide or amino acid residues.

By "origin of replication" is meant a specific region of DNA at which primer production and initiation of DNA polymerase activity begins. In this specification, the term is used to mean a nucleic acid element present on a DNA expression vector that allows the expression vector to increase in copy number within a given host cell.

By "promoter" is meant a genetic element comprising a specific region of DNA at which an RNA polymerase enzyme can bind and begin transcription of a DNA template, thus providing the first step of translating the genetic information contained in the sequence of a nucleic acid into the production of a protein of an amino acid sequence corresponding to that nucleic acid sequence.

By "expression", "gene expression" or "protein expression" is meant the production of protein from information contained within a gene by a host organism.

By "transformation" is meant a biochemical method of inducing a host cell to internalize a nucleic acid molecule. Such nucleic acid molecules are usually genetic elements comprising at least an origin of replication, a selectable marker gene, and a promoter for expression of the selectable marker gene within the host cell.

By "heterologous" is meant not of the same species. Thus, an enzyme expressed in a heterologous host cell is produced in a host cell of a different species than the one from which the enzyme was originally derived.

By "gene" is meant a nucleic acid region having a nucleotide sequence that encodes an expressible protein or polypeptide. A gene may comprise one or more "coding sequences" containing codons that correspond to amino acid residues of the expressed protein; the gene may also comprise, but need not comprise, one or more "non-coding" nucleotide sequence regions that do not contain codons corresponding to amino acid residues of the expressed protein.

All of the biochemical techniques, used for construction and evaluation of the MMLV-RT expression vectors including, but not limited to, restriction digestion protocols, gel electrophoresis, Southern blot, and DNA modification reactions, are known to those of ordinary skill in the art and are described in Sambrook et al., supra, which was previously incorporated by reference herein. In addition, many of these techniques are described in PCT Publication No. WO 95/27067, entitled "Purified DNA Polymerase from *Bacillus stearothermophilus.*"

I. Construction of the Cloning Vector a. Plasmid pUC18N (FIG. 1A)

Plasmid pUC18 (Life Technologies, Inc., Bethesda, Md.) was used as the parent vector. Clones were screened by restriction mapping techniques on agarose gels; such techniques are well known in the art. An Nco I restriction site was introduced between the lac Z ribosome binding site and the Eco RI restriction site of pUC18 by making a substitution of two nucleotide bases, as shown in FIG. 1B. The mutations were introduced using the two synthetic oligonucleotides shown in FIG. 2 as oligonucleotides 1 and 2 (SEQ ID NO: 1 and 2 Respectively). As shown, the oligonucleotides overlap by 30 base pairs at their 3' ends. The oligonucleotides were allowed to hybridize, filled in using the Klenow fragment of *E. coli* DNA polymerase I, and digested with Pvu II and Eco RI. Plasmid pUC18 was digested with Eco RI and partially digested with Pvu II to yield two DNA fragments: a larger fragment including the intact ampicillin resistance gene (Amp), the origin of replication (Ori), and part of the lac Z gene. The smaller Eco RI-Pvu II fragment consisted of the portion of the lac Z gene corresponding to positions 450 to 628 of the pUC18 map. The synthetic Eco RI-Pvu II fragment was inserted into the larger vector fragment, ligated and used to transform E. coli strain JM 109. Clones containing properly constructed vectors produced a blue color using an X-gal substrate (5-bromo-4-chloro-3-indolyl-β-D-galactoside) as a substrate, indicating that the lac Z gene had been properly reconstructed. These results were further verified by restriction mapping. This vector was named pUC18N. (See FIG. 1).

b. Construction of Plasmids Containing the Reverse Transcriptase Gene.

Figure 5:
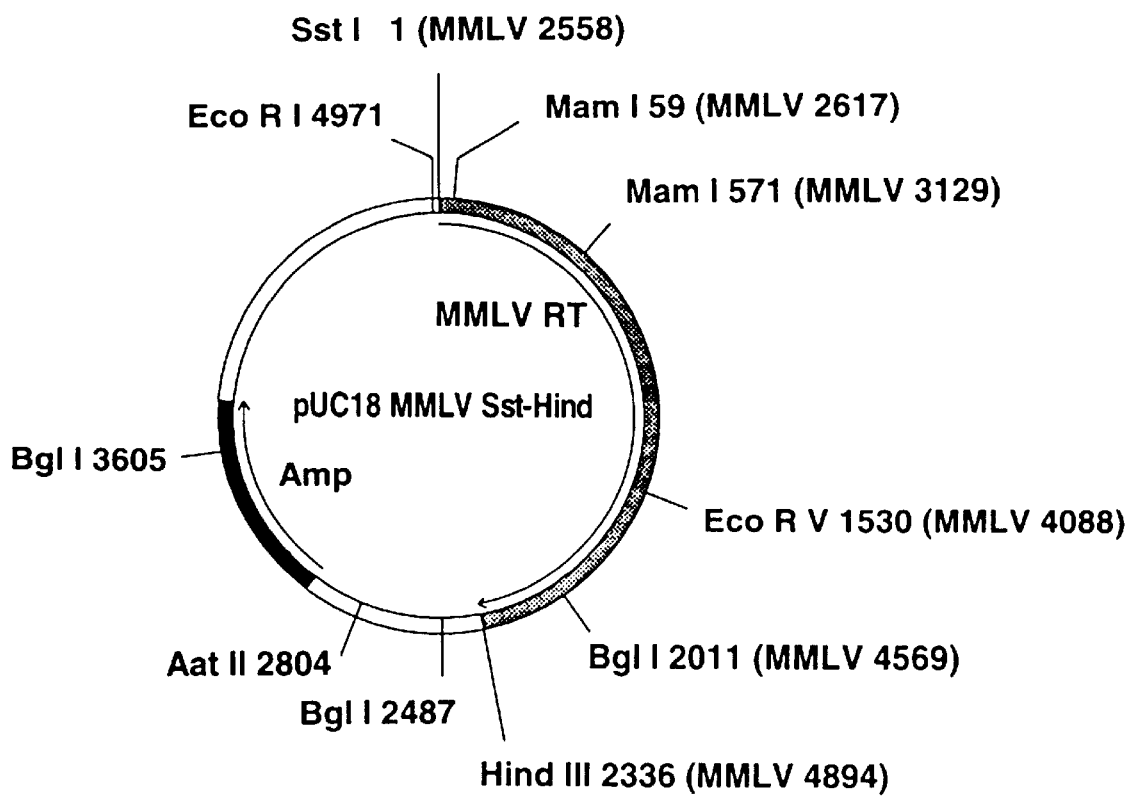
FIG. 5: Construction of plasmid pUC18 MMLV Sst-Hind.
Figure 6:
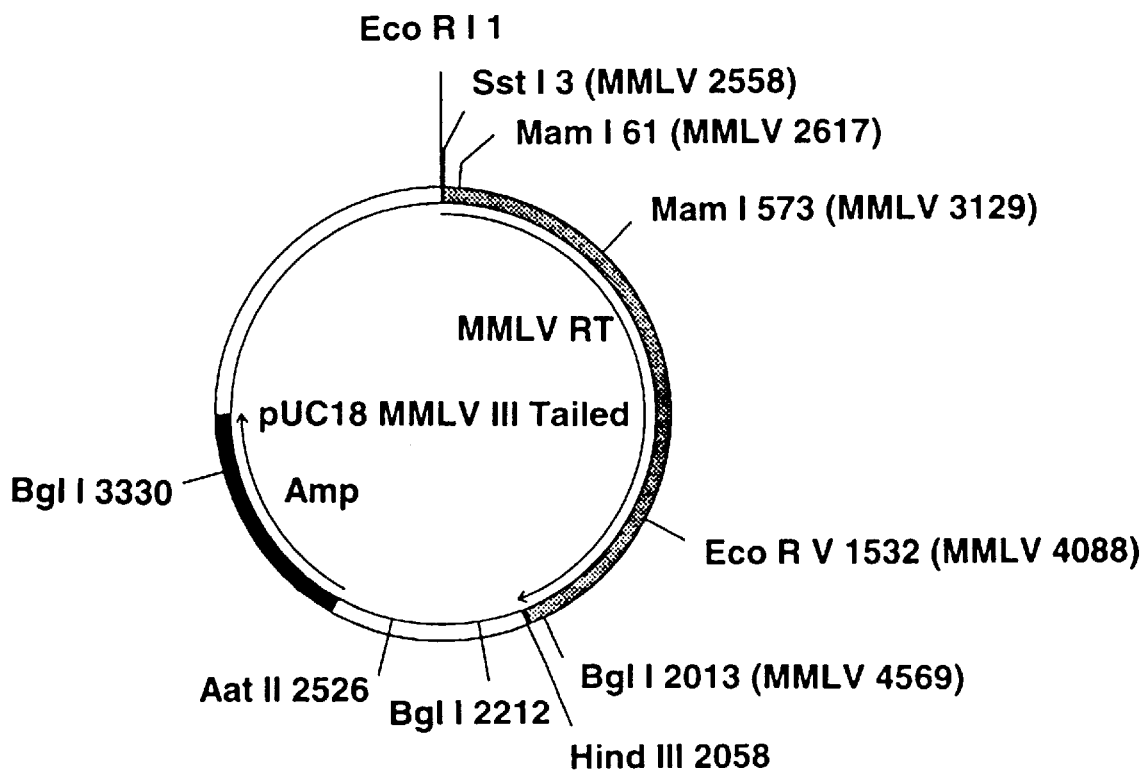
FIG. 6: Construction of plasmid pUC18 MMLV III Tailed.

The intact MMLV gene was isolated as an Sst I-Hind III fragment from the pMMLV-L clone described in Miller and Verma, *J. Virol.* 49:214–222 (1984). This fragment contained the nucleotide sequence corresponding to the region from MMLV position 2558 (Sst I site) to position 4894 (Hind III site) and contained the entire RT gene between 40 extra upstream bases and 284 extra downstream bases. Plasmid vector pUC18 was digested with Sst I and Hind III, and the vector and RT gene were ligated together and used to transform competent *E. coli DH*5 f′ cells. The resulting plasmid was named pUC18 MMLV Sst-Hind (FIG. 5).

This plasmid was then digested with Eco RI and Bgl I, yielding a 2013 bp fragment of the MMLV-RT gene lacking the terminal 3′ sequences of the RT gene. The RT gene fragment was ligated at its Bgl I site to a double-stranded linker designed with Bgl I-Hind III overhangs (FIG. 7) from two synthetic oligonucleotides 8 and 9 (SEQ ID NOS:10 and 11, respectively). The synthetic linker contained the coding sequences for the carboxyl terminus of MMLV reverse transcriptase and a stop codon. Plasmid pUC18 was digested with Eco RI and Hind III, and the large vector fragment was gel purified and ligated with the reconstructed RT gene. The resulting plasmid was called pUC18 MMLV III Tailed, and contained the MMLV gene with the extra 3′ sequences removed.

c. Constriction of pUC18N MMLV Gly and pUC18N MMLV Gly Tet(−).

Figure 8A:
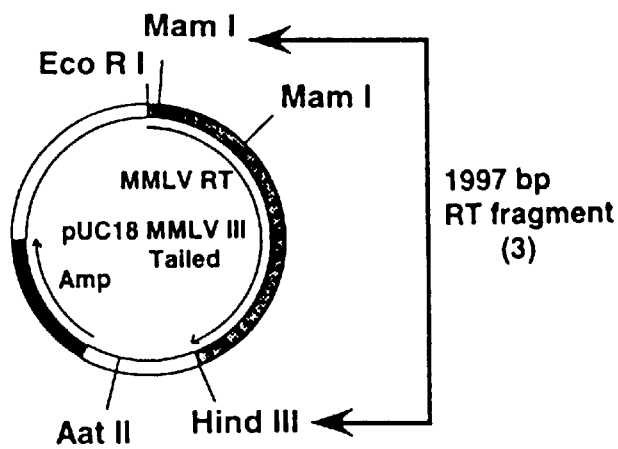
FIGS. 8A to 8F: Construction of plasmids pUC18N MMLV III Gly and pUC18N MMLV Gly Tet(–).
Figure 8B:
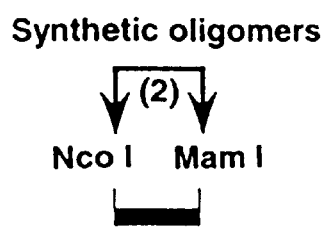

The extraneous 5′ sequences of the cloned RT gene were removed as follows. A 1997 bp Mam I-Hind III fragment was isolated from pUC18N MMLV III Tailed (fragment (3) in FIG. 8A). This nucleic acid fragment contained the RT gene without the 5′ twenty-three nucleotides of the MMLV-RT gene sequence. Two complementary oligonucleotides were synthesized and hybridized to recreate the 5′ portion of the RT gene (fragment (2) in FIG. 8B) (but with nucleotides coding for a glycine in the second amino acid position and a Nco I 5′ overhang containing an initiation codon, as shown below.

Figure 8C:
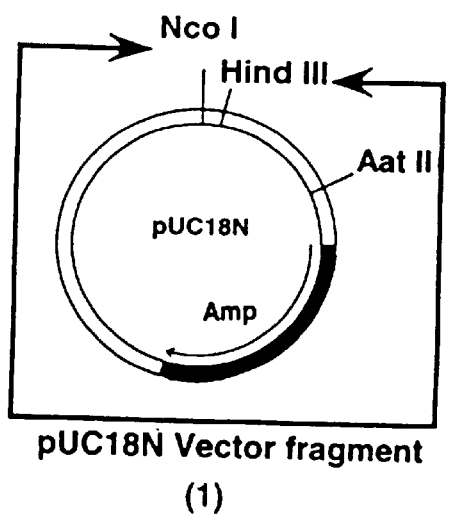
Figure 8D:
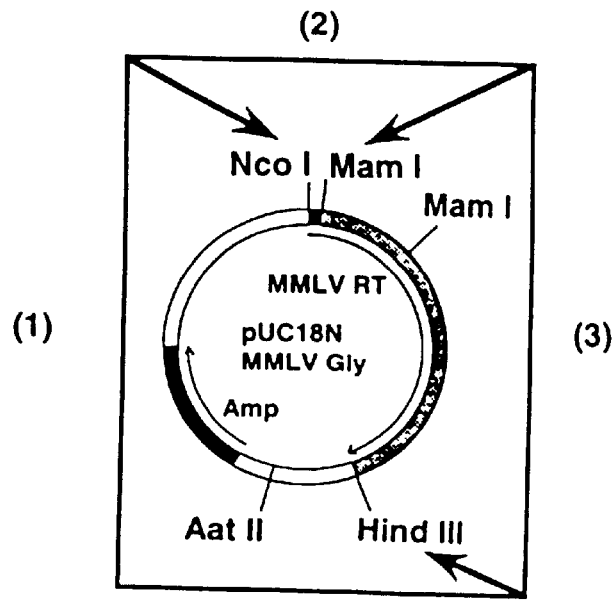
Figure 8E:
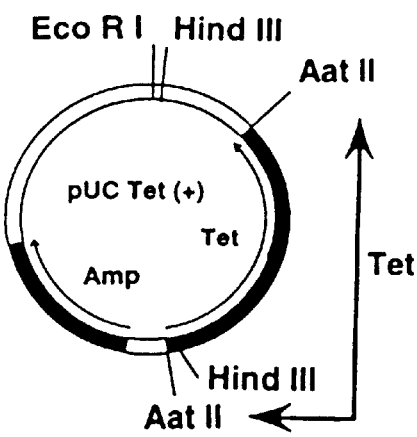
Figure 8F:
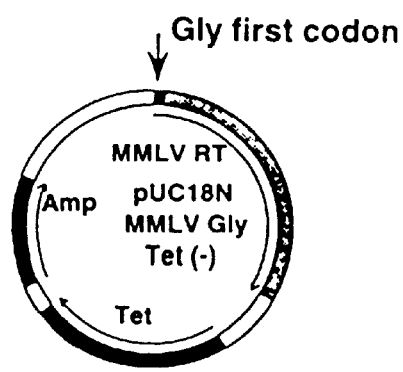

I-Hind III gene was then inserted as well, yielding the expression vector pUC18N MMLV Gly (FIG. 8D). The Tet gene from pUC18 Tet(+) (FIG. 8E), constructed as described below, was inserted at the Aat II site, and the resulting plasmid was called pUC18N MMLV Gly Tet(−) (FIG. 8F). The minus sign refers to the orientation of the Tet gene within the vector.

The cloned MMLV-RT of the present invention differs from the native enzyme in two respects. First, the codon encoding the threonine residue which occupies position 1 of the native enzyme (the second codon of the RT gene) has been replaced with a glycine codon in the cloned RT of the present invention; secondly, the codons for the leucine, asparagine and isoleucine residues occupying amino acid positions 2, 3 and 4 of the mature native protein sequence were replaced with codons more preferred by *E. coli*. The CTA codon coding for leucine was replaced with degenerate codon CTG; the AAT codon coding for asparagine was replaced with degenerate codon AAC, and the ATA codon coding was replaced with degenerate codon ATC. (See Wada, K. et al., *Nucl. Acids Res.* 19(supp.):1981–1986 (1991)).

d. Construction of Plasmid pUC18N SD9D

In order to optimize the expression of cloned MMLV-RT, the lac Z ribosome binding site (RBS) of pUC18N was modified to contain 9 bases complementary to *E. coli* 16S rRNA rather than on the 4 such bases present in the pUC18 parent vector. At the same time, plasmids were constructed having spacer regions separating the RBS and the ATG initiation codon by either 7, 8, or 9 base pairs, as shown for one of the strands in FIG. 3 as SD7, SD8 and SD9. Common elements in the design of these spacer sequences were 1) adenosine (A) in the third position 5′ to the ATG initiation codon (i.e., A at −3 position), 2) no guanine (G) or cytosine (C) in the spacer region except in the Nco I site (CCATGG), and 3) an 5′-RRTTTRR-3′ sequence spanning the RBS and the spacer, where T is thymine and R is a purine nucleotide and A or T is between the RBS and ATG. These common elements for heterologous gene expression were suggested in Jay et al., *Proc. Natl. Acad. Sci. USA* 78:5543–48 (1981) and Jespers et al., *Protein Engineering* 4:485–92 (1991).

The oligonucleotides used to introduce these modifications are shown in FIG. 4. Oligonucleotides 5, 6 and 7, respectively (SEQ ID NO:5, 6 and 7) were each used in conjunction with oligonucleotide 1 (SEQ ID NO: 1), shown in FIG. 2. Oligomers 6 and 7 are identical to Oligomer 5 except as indicated in FIG. 4. Oligomers 5, 6 and 7 were used with Oligomer 1 as in the construction of pUC18N. The nucleotide 4 bases on the 5′ side of the ATG start codon of oligonucleotide 6 and the 4 and 5 bases on the 5′ side by the ATG start codon in oligonucleotide 7 were synthesized with a mixture of A and T since neither was theoretically preferred. See Jespers, et al., supra. As in the construction of pUC18N, a 30 base pair region of complementarity existed

```
Oligonucleotide #3 CATGGGTCTG AACATCGAAG ATGA      (SEQ ID NO:3)

Oligonucleotide #4 TCATCTTCGA TGTTCAGACC           (SEQ ID NO:4)

5'-CATGGGTCTGAACATCGAAGATGA-3'
   3'-CCAGACTTGTAGCTTCTACT-5'
```

Plasmid pUC18N was digested with Nco I and Hind III, and the smaller of the two resulting fragments was removed. The hybridized oligonucleotides (SEQ ID NO:3 and 4) were ligated to the larger pUC18N fragment (fragment (1) in FIG. 8C) at the Nco I site, and the 1992 bp MMLV-RT Mam between oligonucleotide 1 and each of oligonucleotides 3, 4 and 5. As before, each pair of oligonucleotides was allowed to hybridize, was filled in using the Klenow fragment of *E. coli* DNA polymerase I, digested with Pvu II and Eco RI and inserted into the same large pUC18 Pvu II-Eco RI fragment used in constructing pUC18N. The MMLV-RT gene was then cloned into this vector as a Nco I-Hind III fragment as described below.

These constructs were evaluated by measuring the levels of MMLV-RT expression. The cells containing the plasmid with the 9-base spacer (SD9; oligonucleotide 7 SEQ ID No: 7) displayed the highest level of reverse transcriptase expression. The plasmid was isolated and sequenced; both of the degenerate nucleotides 4 and 5 bases on the 5' side of the ATG start codon were found to be adenosine (A) residues. The expresssion vector was named pUC18N SD9D.

e. Insertion of the Tetracycline Resistance Gene

The ampicillin resistance (β-lactamase) gene of pUC18 was used as a genetic selection marker in the early vector constructions. However, owing to the fact that β-lactamase acts to destroy the antibiotic relatively quickly, there may be a sizable plasmid-minus revertant population in a culture in which ampicillin is the sole selective criterion.

In order to tightly regulate the cell population in the cultures, the vector was modified to contain a tetracycline resistance gene. Because tetracycline acts to block cellular uptake of the antibiotic rather than inactivating it, the culture should be more stable in the presence of tetracycline than with ampicillin.

The tetracycline resistance gene was isolated from pBR322 as a 1427 bp Eco RI-Ava I fragment. The single strand overhangs were filled in using the Klenow fragment of *E. coli* DNA polymerase I, yielding a blunt-ended fragment. Aat II linkers were ligated to the tetracycline resistance gene fragment, and digested with Aat II. Plasmid pUC18 was digested with Aat II, and the linearized vector was ligated to the Aat II fragment containing the tetracycline resistance gene. The ligation mixture was used to transform competent *E. coli* JM109 cells, and the transformants were selected by tetracycline resistance. The structure of the plasmid was verified by restriction mapping. Clones were selected having the tetracycline resistance gene inserted in both orientations; the plasmids were named pUC Tet(+) and pUC Tet(−).

The two plasmids were used as a supply of the tetracycline resistance gene (Tet) for insertions into plasmids containing cloned MMLV reverse transcriptase. This approach was preferable to attempting to insert the reverse transcriptase gene(RT) into a vector already containing the Tet gene, since the Tet gene contains restriction sites for enzymes used in the reverse transcriptase cloning, while the RT gene contains no Aat II sites.

f. Construction of pUC18N SD9D MMLV Gly and pUC18N SD9D MMLV Gly Tet(−).

Figure 9A:
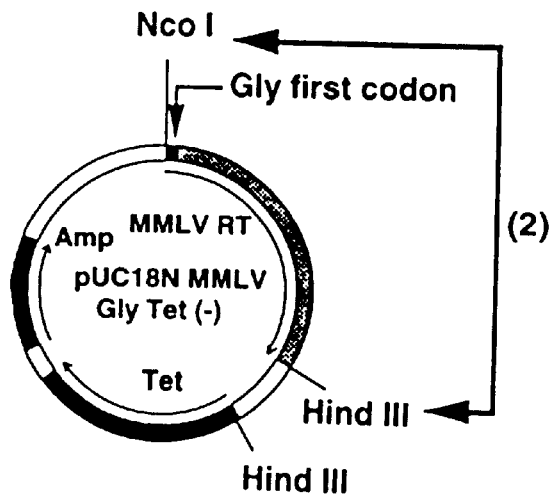
FIGS. 9A to 9E: Construction of plasmids pUC18N SD9D MMLV Gly and pUC18N SD9D MMLV Gly Tet(–).
Figure 9B:
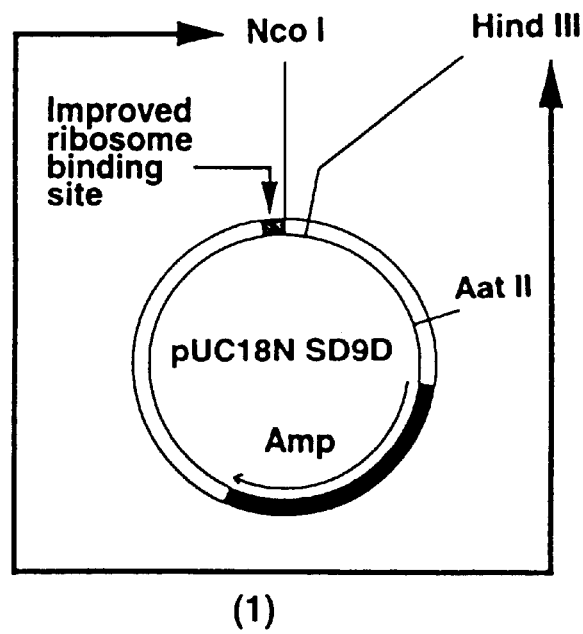
Figure 9C:
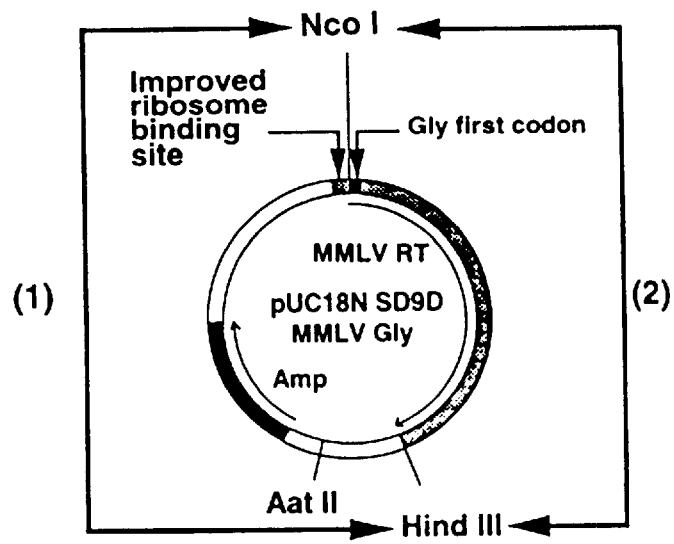
Figure 9D:
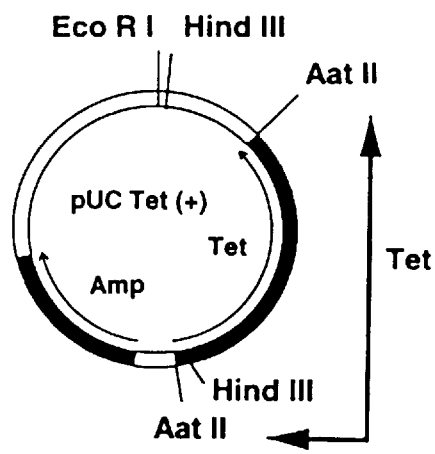
Figure 9E:
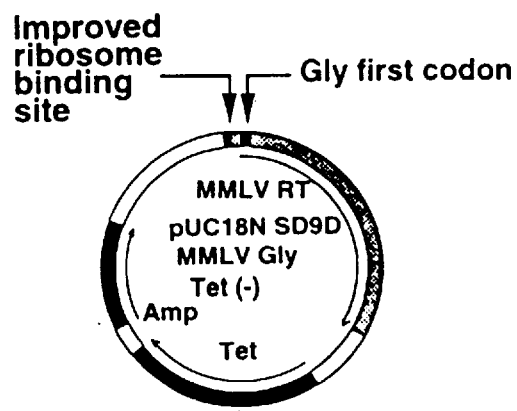

The intact, modified reverse transcriptase gene from pUC18N MMLV Gly Tet(−) was isolated as a 2018 bp Nco I-Hind III fragment (fragment (2) in FIG. 9A) and ligated with vector pUC18N SD9D from which the Nco I-Hind III polylinker region had been removed (fragment (1) in FIG. 9B). The resulting plasmid, called pUC18N SD9D MMLV Gly (FIG. 9C), contained the MMLV-RT gene modified in the three ways described above in addition to having the improved ribosome binding site and spacer region, as described above. This plasmid was cleaved at its unique Aat II site, and the Aat II Tet gene fragment from pUC18 Tet(+) (FIG. 9D) was inserted into the vector and ligated. Plasmids containing the Tet gene insert were isolated in both possible orientations, and the level of RT expression was tested for clones containing each plasmid. The clone having the Tet gene in the (−) orientation (with the coding strand in the same orientation as MMLV-RT); FIG. 9E was found to produce higher levels of RT than the clone having the Tet gene in the opposing orientation and was therefore chosen as the preferred clone.

II. Selection of the Host Cell Strain

The following *E. coli* strains were tested for expression and purification of MMLV-RT: JM109, DH5 f', XL1 Blue (Stratagene, San Diego, Calif.), JM105, ER 1458, NM 522, Inv f' (Invitrogen, San Diego, Calif.), TOPP™ strains 1–6 (Stratagene), 1200, MRE 600, Q 13, and A 19. Some of these strains are mutants which are deficient in RNase I (strains 1200, MRE 600, Q 13, and A 19), while others are common laboratory strains. Some of these strains contain the lac I$^q$ repressor and required induction with isopropylthiogalactoside (IPTG). The level of RT expression of host cells containing the RT gene was estimated by visualization of the resulting protein on SDS-polyacrylamide gels and also, in most cases, by enzyme activity assays on crude cell lysates. Of the RNase I deficient strains, *E. coli* 1200 (Yale University *E. coli* Genetic Stock Center, Strain 4449) consistently showed high levels of enzyme expression using these assays; unless indicated otherwise, all experiments described herein were conducted using this strain.

III. Growth of *E. coli* 1200 containing pUC18N SD9D MMLV Gly Tet(−)

The fermentation culture medium (A–Z Amine media) contained the following components in a volume of 200 liters:

| | |
|---|---|
| N-Z Amine A (Sheffield Products, Norwich, N.Y.) | 2 kg |
| Yeast Extract (Difco) | 1 kg |
| NaCl | 1 kg |
| NaOH | 8 g |
| Tetracycline (12 mg/ml in 70% ethanol) | 200 ml |

The mixture was autoclaved in the fermentation vessel at 121° C. for 20 minutes, then allowed to cool. The tetracycline was added when the temperature reached 37° C.

The inoculum of *E. coli* 1200 containing pUC18N SD9D MMLV Gly Tet(−) was prepared by inoculating 2 ml of N–Z Amine plus 12 μg/ml tetracycline (LB+Tet) with a frozen stock culture of the vector-containing strain and incubating overnight at 37° C. with shaking. The resulting 2 ml culture was then used to inoculate 20 one-liter cultures, which were again incubated overnight at 37° C. with shaking.

The 200 liter fermenter was then inoculated with 20 liters of seed culture, and the cells were allowed to grow at 37° C. until 30 minutes after the culture had reached maximum density as determined by measuring light attenuation at a wavelength of 660 nm. This generally occurs about 7.5 hours after inoculation. During incubation the culture was stirred continuously at 150 RPM for the initial 3 hours and then at 180 RPM thereafter. The vessel was sparged with air at 45 l/min. The pH of the medium was not controlled during fermentation, and rose during that time to approximately 8.2.

The culture was chilled to 20° C., and the cells were collected by centrifugation in a Sharples centrifuge. The cells were not washed. The cell paste was divided into 200 g portions and frozen in liquid $N_2$. During freezing, the cell mass was broken into smaller pieces to ensure rapid and thorough freezing. The frozen cell paste was then stored at −70° C.

IV. Purification of MMLV Reverse Transcriptase from *E. coli* 1200/pUC18N SD9D MMLV Gly Tet(−)

1. Assay of Reverse Transcriptase Activity and Protein Concentration.

Methods for assaying reverse transcriptase activity are known in the art. For the work described here, the dT:rA assay described by Kacian was used (Kacian, *Methods for Assaying Reverse Transcriptase*, in *Methods in Virology* (Academic Press 1977), herein incorporated by reference as part of this disclosure). One unit of reverse transcriptase activity converts 1 nmole of dTTP to acid-precipitable form in 10 minutes under the conditions described therein.

2. Cell Lysis

Eleven hundred grams of frozen cell pastes were broken into pieces and suspended in 3.3 liters of Lysis Buffer (25 mM Tris-HCl (pH 7.5), 10 mM ethylenediamine tetraacetic acid (EDTA), 10% (v/v) glycerol, 5 mM dithiolthreitol (DTT), 1% (v/v) Triton X-100, 10 mM NaCl, 1 mM phenylmethylsufonyl fluoride (PMSF)) by stirring at 4° C. The cells were then lysed by 2 passes through an APV Gaulin 15MR homogenizer at a continuous pressure of 8,000 psi. The receiving vessel was kept in an ice water bath, and the initial homogenate was allowed to chill for 30 minutes prior to the second pass. The lysate was then cleared by centrifugation at 4,500×g for 1 hour at 4° C., and the pellet was discarded. The clarified lysate was either used immediately or stored frozen at −70° C. and brought to 4° C. before use.

3. Phosphocellulose Column Chromatography

Phosphocellulose (Whatman P11, 100 g) was treated with 2.5 liters of 0.5 N NaOH, followed by 2.5 liters of 0.5 N HCl, as recommended by the manufacturer. After a final water wash, the phosphocellulose was suspended in 1.0 l of 1.0 M Tris-HCl (pH 7.5), allowed to stand for 5–10 minutes, and transferred to a Buchner funnel. The buffer was removed by vacuum filtration, and the phosphocellulose was washed with 1.0 M Tris-HCl (pH 7.5) until the pH of the effluent matched the pH of the wash solution. The phosphocellulosle was transferred to a beaker and suspended in 1.0 l of column buffer (25 mM Tris-HCl (pH 7.5), 1 mM EDTA, 10% (v/v) glycerol, 1 mM DTT, 0.1% (v/v) Triton X-100 and 1 mM PMSF) containing 0.05 M NaCl. After 5–10 minutes the buffer was removed under vacuum filtration as described above. The phosphocellulose was then suspended in 700 ml column buffer containing 0.05 M NaCl and cooled to 4° C.

All subsequent steps were carried out at 4° C. The chromatography was carried out using Pharmacia FPLC equipment. A Pharmacia XK 50/30 (5.0 cm×26.0 cm) was packed with the washed and equilibrated phosphocellulose to give a bed of 500 ml. The column was then washed with 1 l of column buffer containing 0.05 M NaCl at a flow rate of 60 ml/hour. Column adapters (Pharmacia AK 50) were used to minimize the dead volume at the ends of the column. Six hundred ml of clarified cell lysate were applied to the column at a flow rate of 30 ml/hour. The column was then washed with 650 ml of column buffer containing 0.2 M NaCl at the same flow rate. Because of shrinkage of the column bed, excess buffer was removed from the space above the column bed, and the top flow adapter was readjusted to maintain contact with the bed surface.

The column was eluted with a 1500 ml linear salt gradient, from 0.2 M NaCl to 0.7 M NaCl in a column buffer at 30 ml/hour. The effluent was monitored for the presence of protein by its absorbance at 280 nm. Fractions of 25 ml were collected except during the elution of the protein peak, during which 15 ml fractions were collected.

Figure 10:
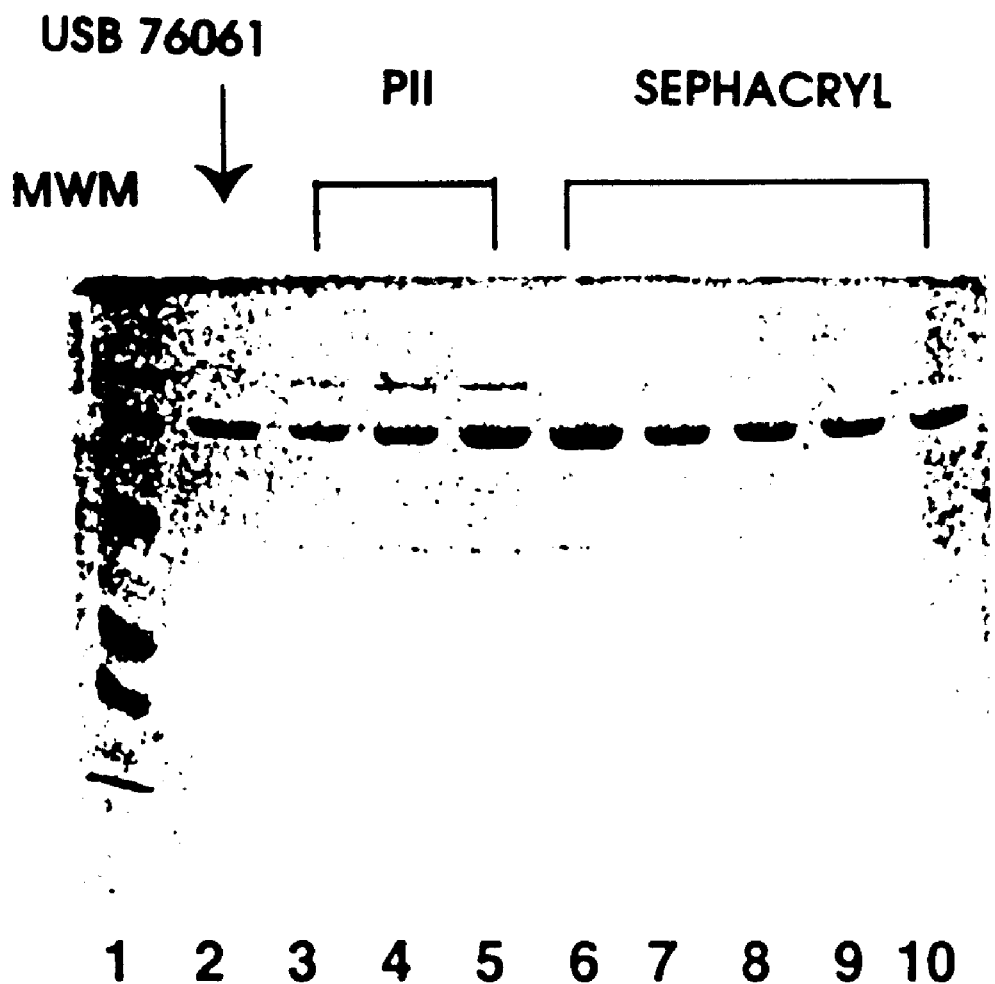
FIG. 10: Sodium dodecyl sulfate polyacrylamide gel electrophoresis (SDS-PAGE) gel photograph of P-11 and Sephacryl S-200 fractions of purified MMLV-RT.

The column fractions were analyzed using SDS-polyacrylamide gel electrophoresis (SDS-PAGE) followed by Coomassie Brilliant Blue staining. SDS-PAGE is well known in the art, and is described in Laemmli, U. K., *Nature* 227:680 (1970), which is hereby incorporated by reference herein. Ten microliters from each fraction were analyzed in each gel lane (FIG. 10, lanes 3–5). A control lane contained a known amount of purified MMLV-RT (FIG. 10 lane 2).

Those fractions containing a significant amount of protein migrating with an apparent molecular weight similar or identical to that of the MMLV-RT control and which contained little visible contaminating protein bands were pooled. Approximately 95% of the protein eluting within the major protein peak was able to be pooled without including a significant amount of contaminating proteins. Activity assays may also be used to locate and pool the peak MMLV-RT enzyme fractions; such procedures are known to those of ordinary skill in the art.

4. Sephacryl S200 Gel Filtration

The pooled phosphocellulose fractions, having a volume of 80–100 ml, were concentrated to less than 25 ml by ultrafiltration in an Amicon ultrafiltration cell using an Amicon P30 membrane at 20 psi of nitrogen. Two 2.6 cm×94 cm Pharmacia XK 26/100 columns were packed with Sephacryl S200 (Pharmacia) according to the manufacturer's directions. Column adapters were used to minimize the dead volume. Both columns were connected in series. The columns were washed with 2 l column buffer containing 0.2 M NaCl at a flow rate of 90 ml/hour. The concentrated phosphocellulose pool (about 25 ml) was loaded onto the upstream column, and the column was developed with the same buffer at a flow rate of 90 ml/hour. Again, the effluent was monitored for its absorbance at 280 nm; the initial 200 ml of effluent was collected in a single pool, and 4 ml fractions were collected during the elution of the protein peak. The MMLV-RT eluted when approximately 290–300 ml of buffer had been applied to the columns.

The fractions were again analyzed using SDS-PAGE as above. Three microliters from each fraction in the peak region were run in each gel lane (FIG. 10, lanes 6–10); as before, a control lane contained purified MMLV-RT of a known mass. Those fractions containing a significant amount of protein migrating with the purified MMLV-RT and which contained little visible contaminating protein were pooled. Preferably, those fractions containing predominant bands of a higher apparent molecular weight than the MMLV-RT were not included in the pool. Between 95–98% of the protein in the major S200 peak was included in the pool. Although assays for reverse transcriptase activity may be used to locate and identify the MMLV-RT in the fractions, analysis preferably includes SDS-PAGE to avoid including higher molecular weight contaminants in the pool.

The pooled S200 fractions are sufficiently concentrated for most uses. The enzyme can be stored in 50% glycerol at −20° C.

EXAMPLE 1

Expression of MMLV-RT by *E. coli* containing pUC18N MMLV Gly Tet(−) or pUC18N MMLV Gly Tet(−) with a Modified Ribosome Binding Site and Spacer Sequences of Different Lengths The MMLV-RT gene containing the glycine amino acid substitution in the first position was evaluated in vector pUC18N and pUC18N with the spacers and modified ribosome binding site described above. All vectors contained the Tet gene and were evaluated in *E. coli* strain 1200.

Fifty ml cultures of *E. coli* 1200 containing either of these two contructs were grown for 16.5 hours at 37° C. with shaking. Aliquots of 0.5 ml were harvested, centrifuged for 2 minutes in a microcentrifuge, and the supernatants were discarded. The cell pellets were resuspended on 0.5 ml of a wash buffer (50 mM Tris-HCl (pH 8.0), 10 mM NaCl, 5 mM EDTA and 0.25 M sucrose) and then centrifuged as before. The cell pellets were frozen at −80° C. and then resuspended in 200 μl of lysis buffer (10 mM Tris-HCl (pH 8.0), 10 mM NaCl, 1 mM EDTA 1% glycerol, 5 mM DTT, 0.2 mM PMSF and 100 μg/ml lysozyme) and left on ice for 20 minutes. One hundred microliters of 0.75% (v/v) Triton X-100 was added to each sample, and the mixture was frozen and thawed twice. The lysate was cleared by centrifigation, and total protein was assayed by the method of Read and Northcote (*Anal. Biochem.* 116:53–64 (1981)), the disclosure of which is incorporated by reference herein.

Aliquots of the lysate were assayed for reverse transcriptase activity. The level of reverse transcriptase activity in each clone was calculated in terms of units per microgram of total protein in the lysate, as well as units per ml of bacterial culture. The results shown in Table 1 indicate that the vector containing the modified ribosome binding site (RBS) and the 9 base spacer sequence expressed the highest levels of enzyme.

TABLE 1

Comparison of RT Expression in Different Plasmid Constructs

| Expression Vector | RT activity; U per μg total protein | RT activity; U per ml culture |
| --- | --- | --- |
| unmodified pUC18N | 1.81 | 746 |
| pUC18N with 7 base spacer and improved RBS | 2.25 | 823 |
| pUC18N with 8 base spacer and improved RBS | 1.72 | 679 |
| pUC18N with 9 base spacer and improved RBS | 2.69 | 1,036 |

EXAMPLE 2

Comparision of Modified MMLV-RT in *E. coli* 1200 and JM 109 Host Strains

Plasmid pUC18N was used to create plasmids encoding MMLV-RT with glycine, alanine, or valine substitutions in the first native amino acid position. These substitutions were created using oligonucleotides similar to oligos 3 and 4, but with a codon of sequence 5'-GTT-3' or 5'-GCT-3' (coding for valine or alanine respectively) in the second position of the RT gene, following the initiation codon. The Tet gene from pUC18 Tet(+) was inserted into the resulting plasmids in each orientation for comparison. These plasmids were used to transform *E. coli* JM109 host cells which contain an episomal copy of the lac repressor lac $I^q$ gene. The transformant cells were grown overnight as in Example 1, except when the cells reached log phase growth, the lac promoter was induced by the addition of 0.5 mM (IPTG) for approximately 22 hours. Aliquots were harvested and assayed for reverse transcriptase activity as in Example 1. The results are shown in Table 2 below. As can be seen, the Gly Tet(–) construction showed the highest level of enzyme expression.

TABLE 2

Effect of Orientation of Tet gene on RT Activity

| | RT Activity; U per μg Total Protein | RT Activity; U per ml Culture |
| --- | --- | --- |
| Gly Tet (+) | 0.44 | 177 |
| Gly Tet (–) | 1.29 | 472 |
| Ala Tet (+) | 0.59 | 229 |

TABLE 2-continued

Effect of Orientation of Tet gene on RT Activity

| | RT Activity; U per μg Total Protein | RT Activity; U per ml Culture |
| --- | --- | --- |
| Ala Tet (–) | 0.54 | 243 |
| Val Tet (+) | 0.91 | 400 |
| Val Tet (–) | 1.03 | 395 |

In a separate experiment, the Gly Tet(–) and the Val Tet(–) constructs were evaluated in *E. coli* hosts 1200 and JM 109. The JM 109 cultures were induced as above, while the 1200 cultures were uninduced. The results shown below in Table 3 indicate that the levels of expression in both strains are comparable for the Gly substituted MMLV-RT, and higher in strain 1200 for the Val substituted plasmid.

TABLE 3

Comparison of RT Expression in Different Host Cell Strains

| | RT Activity; U per μg Total Protein | RT Activity; U per ml Culture |
| --- | --- | --- |
| 1200/Gly Tet (–) | 1.04 | 591 |
| JM 109/Gly Tet (–) | 1.05 | 533 |
| 1200/Val Tet (–) | 1.00 | 516 |
| JM 109/Val Tet (–) | 0.61 | 357 |

EXAMPLE 3

Growth of *E. coli* 1200/pUC18N SD9D MMLV Gly Tet(–) and Expression of MMLV-RT

One liter of growth medium contained 10 g of N–Z Amine A, 5 g of yeast extract, 5 g of NaCl, and 0.1 ml of 10 N NaOH. One milliliter of 12 mg/ml tetracycline in 70% ethanol was added to the cooled, autoclaved medium.

Two ml of medium was inoculated from a frozen stock culture of the *E. coli* transformant. This was allowed to grow overnight with shaking at 37° C. The two ml bacterial culture was used to inoculate 500 ml of medium, and this culture was grown overnight as above. The 500 ml culture was, in turn, used to inoculate 5 liters of medium in a New Brunswick BioFlo III fermenter. The culture was grown at 37° C. with stirring at 350 RPM. The culture was sparged with air at 4 liters/minute during fermentation. Five to ten milliliter samples were taken every hour for measurement of pH, optical density, protein concentration and reverse transcriptase activity. These results are shown in Table 4 below.

TABLE 4

Growth Kinetics of 1200/pUC18N SD9D MMLV Gly Tet(–)

| Sample | Time(hr) | pH | A600 | Protein (mg/ml) | RT Activity; U/Assay | RT Activity; U/mg Protein |
| --- | --- | --- | --- | --- | --- | --- |
| 1 | 0* | 6.93 | 0.00 | 0.00 | 0.00 | 0 |
| 2 | 0** | 7.15 | 0.29 | 0.06 | 1.17 | 2920 |
| 3 | 1 | 7.14 | 0.22 | 0.18 | 0.91 | 2270 |
| 4 | 2 | 6.97 | 0.69 | 0.07 | 0.51 | 1270 |
| 5 | 3 | 6.91 | 0.96 | 0.11 | 0.87 | 2170 |
| 6 | 4 | 7.02 | 1.72 | 0.09 | 0.92 | 2300 |
| 7 | 5 | 7.40 | 2.16 | 0.13 | 0.60 | 1510 |
| 8 | 6 | 7.70 | 2.50 | 0.11 | 1.27 | 3180 |

TABLE 4-continued

Growth Kinetics of 1200/pUC18N SD9D MMLV Gly Tet(-)

| Sample | Time(hr) | pH | A600 | Protein (mg/ml) | RT Activity; U/Assay | RT Activity; U/mg Protein |
|---|---|---|---|---|---|---|
| 9 | 7 | 7.83 | 2.91 | 0.12 | 1.49 | 3720 |
| 10 | 8 | 7.98 | 2.79 | 0.09 | 1.46 | 3660 |

*Pre-Inoculation
**Post-Inoculation

EXAMPLE 4

Large-Scale Purification of Cloned MMLV-RT

The enzyme was prepared as described in Example 1 above. Volumes of reagents were adjusted in proportion to the weight of the pelleted cells at the beginning of the procedure. As indicated in Table 5, high purified enzyme was recovered with a 48% yield.

TABLE 5

Purification Parameters: MMLV-RT Purification Scale-Up

| Fraction | Volume (ml) | Protein (mg) | Total Activity (U) | Specific Activity (U/mg) | Yield (%) |
|---|---|---|---|---|---|
| Crude Lysate | 605.6 | $2.1 \times 10^4$ | $1.5 \times 10^8$ | 7,100 | 100 |
| P-11 Pool | 15.2 | 741 | $8.2 \times 10^7$ | 110,656 | 52 |
| Sephacryl Pool | 79 | 363 | $7.9 \times 10^7$ | 217,400 | 48 |

EXAMPLE 5

SDS-PAGE of Purified MMLV-RT from 1200/pUC18N SD9D MMLV Gly Tet(-) Clone

The progress of the purification was monitored by SDS-PAGE analysis of protein in the P-11 pool and the Sephacryl pool of Example 4 above. SDS-PAGE was conducted in a 10% reducing gel essentially as described in Laemmli, supra. Samples were prepared as follows. An aliquot of the P-11 pool was diluted 50-fold into a gel sample buffer (50 mM Tris-HCl (pH 6.8), 10% (v/v) glycerol, 5% β-mercaptoethanol (BME), 2% (w/v) SDS and 0.05% (w/v) bromphenol blue) and heated at 95° C. for five minutes. An aliquot from the Sephacryl column pool was diluted 10-fold with gel sample buffer and heated in the same way. A sample of commercially obtained MMLV-RT (USB, Cleveland, Ohio) was prepared identically. The latter sample was reported by the supplier to have a specific activity of 187,000 U/mg and was provided in an initial concentration of 1500 U/μl. Prestained molecular weight markers (Bio Rad Laboratories, San Rafael, Calif.) were used to estimate the molecular weights of the proteins contained in the sample pools. The apparent molecular weight of the marker proteins were 18,500 Da (egg white lysozyme), 27,500 Da (soybean trypsin inhibitor), 32,500 Da (bovine carbonic anhydrase), 49,500 Da (chicken ovalbumin), 80,000 Da (bovine serum albumin), and 106,000 Da (phosphorylase B from rabbit muscle). The gel was loaded as shown in Table 5, and is shown in FIG. 10.

TABLE 5

Order of SDS-PAGE Samples in MMLV-RT Purification

| Lane | Sample | Volume (μl) |
|---|---|---|
| 3 | P-11 Pool | 2.0 |
| 4 | P-11 Pool | 4.6 |
| 5 | P-11 Pool | 7.0 |
| 6 | P-11 Pool | 10.0 |
| 7 | Sephacryl Pool | 6.5 |
| 8 | Sephacryl Pool | 5.0 |
| 9 | Sephacryl Pool | 4.2 |
| 10 | Sephacryl Pool | 3.3 |

EXAMPLE 6

Contaminating Ribonuclease Activity in a Commercial Preparation of MMLV-RT

A 24 cm×0.4 cm column of Sephadex G75 was equilibrated with the following buffer (1×Column Buffer) 20 mM Tris-HCL (pH 7.6), 0.1 mM EDTA, 200 mM NaCl, 1 mM dithiothrietol (DTT), 0.01% (v/v) Nonidet P-40 and 10% (v/v) glycerol.

RNase assays were performed by using nucleic acid hybridization to measure loss of RNA incubated with the enzyme. Details of the method can be found in Arnold, et al., (U.S. Pat. No. 5,283,174) and in Nelson, et al., (U.S. patent application Ser. No. 08/094,577). Five ml from each enzyme sample were transferred to a test tube. Ten ml of an in vitro synthesized RNA transcript (about 1–4 fmol) in water were added, and the reactions were incubated at 37° C. for 1 hour. Fifty ml of an acridinium ester-labelled DNA probe complementary to a region of the RNA transcript were added in 0.1 M lithium succinate (pH 4.7), 1.1 M lithium chloride, 2% (w/v) lithium lauryl sulphate, 20 mM EDTA, 20 mM ethylene glycol bis (beta-amino ethyl ether) N, N, $N^1$, $N^1$ tetraacetic acid (EGTA), 15 mM Aldrithiol (Aldrich Chemical Company, Milwaukee, Wis.), and the reaction mixture was incubated at 60° C. for 20 minutes. Three hundred ml of a solution of 0.6 M sodium borate (pH 8.5), 1% (v/v) Triton X-100 were added, and the reaction mixture was incubated at 60° C. for 7 minutes to destroy acridium ester present on unlabelled probe. The amount of remaining label was determined in a luminometer.

Similar methods for assessing RNase activity using radiolabel probes or directly measuring degradation of radiolabelled RNA by monitoring conversion from acid-precipitable to acid soluble forms are well known to those skilled in the art and may be used in the practice of the present invention. Other methods for assaying low level RNase activity are available in the scientific literature and their application to the practice of the present invention is easily appreciated by those of skill in the art.

Twenty five microliters of a commercial preparation of MMLV-RT (U.S. Biochemicals, Cleveland, Ohio) was mixed with 12.5 μl of 10×Column Buffer without glycerol, 10 μl of a 10 mg/ml solution of Blue Dextran, and 77.5 μl water. Before use the water was treated with diethyl pyrocarbonate, as described in Sambrook et al., supra, to destroy contaminating RNAses. The enzyme was applied to the column and eluted with Column Buffer at a flow rate of 1.8 ml/hour. Two hundred thirty μl fractions were collected and assayed for reverse transcriptase and RNAse activities, as described above.

The results of two identical column runs are shown in the following table.

TABLE 6

Comparison of Enzyme Activities For Two Different Column Runs

| | Column 1 | | Column 2 | |
|---|---|---|---|---|
| Fraction | RT Activity (RLU) | RNAse Activity (% degraded) | RT Activity (RLU) | RNAse Activity (% degraded) |
| 1 | | | | |
| 2 | 61 | | | |
| 3 | | | | |
| 4 | 1000 | | | |
| 5 | | | | |
| 6 | 2574 | | | |
| 7 | | | | |
| 8 | 1751 | | 1605 | |
| 9 | | | 20029 | |
| 10 | 14328 | 14 | 98216 | 9 |
| 11 | | | | |
| 12 | 143493 | 0 | 40619 | 0 |
| 13 | | | 43523 | |
| 14 | 21570 | 51 | 9299 | 55 |
| 15 | | | 26650 | |
| 16 | 11306 | 0 | 13490 | 17 |
| 17 | | | 1226 | |
| 18 | | | 4713 | |
| 19 | | | 1462 | |
| 20 | 2583 | 64 | 1379 | 57 |
| 21 | | | 1263 | |
| 22 | 913 | 52 | 1072 | 0 |
| 23 | | | | |
| 24 | 907 | 21 | | 44 |
| 25 | | | | |
| 26 | 887 | 56 | | 73 |
| 27 | | | | |
| 28 | 21375 | | | |
| 29 | | | | |
| 30 | 8100 | | | |

As this Table illustrates, the commercial enzyme preparation contains significant endogenous RNAse activity. This RNAse activity is other than the RNAse H activity associated with the MMLV-RT enzyme, since it degrades single-stranded RNA. When analyzed by gel filtration chromatography, at least four peaks of non-RNAse H RNAse activity are obtained. These peaks may represent four distinct enzymes. Alternatively, they may represent aggregation of one or more protein, dissociation of such a protein into subunits, or other chromatographic artifacts. At least one of these peaks of non-RNAse H RNAse activity co-elutes with the MMLV-RT.

EXAMPLE 7

Comparison of Contaminating Ribonucleases in Partially Purified Recombinant MMLV-RT from *E. Coli* Host Cells JM 109 and 1200

In order the compare the amount of contaminating ribonuclease activities present in MMLV-RT-containing cell lysates after P11 column purification between host cells JM 109 and 1200 transformed with plasmid pUC18N SD9D MMLV Gly Tet(−), fractions from each column were assayed for reverse transcriptase activity using the dT:rA assay described in Kacian, *Meth. Virol.* supra, and for non-RNAse H RNAse activity using the assay described in the previous example.

The results obtained for each cell type are shown in the following tables:

TABLE 7

*E. Coli* Strain 1200

| Fraction | RT Activity (RLU) | RNAse activity (% degraded) |
|---|---|---|
| 1 | 1007 | 0 |
| 5 | 1084 | 0 |
| 10 | 1021 | 0 |
| 15 | 3712 | 0 |
| 20 | 38359 | 0 |
| 25 | 20741 | 0 |
| 30 | 316513 | 0 |
| 33 | 346922 | 0 |
| 36 | 504196 | 0 |
| 39 | 387533 | 0 |
| 42 | 371897 | 0 |
| 45 | 472248 | 0 |
| 48 | 1199993 | 0 |
| 51 | 1529015 | 0 |
| 54 | 1126592 | 0 |
| 57 | 1034428 | 0 |
| 60 | 850009 | 0 |
| 63 | 698462 | 0 |
| 66 | 390121 | 0 |
| 69 | 177736 | 0 |
| 72 | 260049 | 0 |
| 76 | | |

TABLE 8

*E. Coli* Strain JM 109

| Fraction | RT Activity (RLU) | RNAse activity (% degraded) |
|---|---|---|
| 1 | 1103 | 0 |
| 5 | 1238 | 0 |
| 10 | 1287 | 0 |
| 15 | 28359 | 29 |
| 20 | 50927 | 75 |
| 25 | 29551 | 70 |
| 30 | 350732 | 83 |
| 35 | 198151 | 30 |
| 38 | 164047 | 54 |
| 41 | 149647 | 66 |
| 44 | 161963 | 62 |
| 47 | 674123 | 81 |
| 50 | 2060603 | 83 |
| 53 | 2703286 | 85 |
| 56 | 1967435 | |
| 59 | 1608490 | 90 |
| 62 | 782936 | 86 |
| 65 | 265569 | 78 |
| 68 | 147948 | 63 |
| 71 | 78481 | 38 |
| 74 | 44426 | 3 |
| 77 | 19964 | 0 |
| 81 | 13900 | 0 |

The data show that the enzyme prepared from JM 109 cells contained significant amounts of non-RNAse H ribonuclease activity throughout the P11 column profile. Significant amounts of RNAse activity eluted with the reverse transcriptase activity. In contrast, the reverse transcriptase purified from the *E. coli* 1200 cells was free of detectable contaminating RNAse activity after the crude extract was purified by phosphocellulose column chromatography.

EXAMPLE 8

Amplification of Mycobacterium tuberculosis Ribosomal RNA Target Sequence Using Purified Recombinant MMLV Reverse Transcriptase from *E. coli* 1200/pUC18N SD9D MMLV Gly Tet(−)

Nucleic acid amplification was performed using the procedure described in Kacian and Fultz, EPO 0 408 295 A2, which is incorporated by reference herein and which enjoys common ownership with the present application. A reagent mixture was made up as follows: 768 microliters of water was given, in order, 25 µl 1 M Tris-HCl (pH 8.0), 50 µl 1 M MgCl$_2$, 44 µl KCl, 500 µl 40 mM rNTPs, 500 µl 10 mM dNTPs, 9 µl T7 promoter-primer (84 pmoles/µl), and 5 µl non-T7 primer (150 pmole/µl) and mixed. The volume of this mixture (Solution A) was calculated to be suitable for 50 assays. Forty µl of solution A was added to each reaction tube. Ten microliters of the purified target rRNA (0.05–25 fg/µl diluted in Template Dilution Buffer (0.2% (w/v) bovine serum albumin in 150 mM NaCl)) was added to each tube. The target rRNA had nucleic acid sequences sufficiently complementary to the primer and the promoter-primer to allow hybridization to occur under stringent hybridization conditions. Preporation of rRNA is known to those of skill in the art. Two hundred microliters of silicone oil was layered onto the surface of each reaction mixture, and the reaction tubes were heated at 95° C. for 15 minutes in a heating block. The reaction tubes were then transferred into a 42° C. water bath and allowed to cool for 5 minutes.

An enzyme mixture was prepared by transferring 46.8 µl Dilution Buffer to a tube and adding 1.1 µl (900 U) MMLV-RT and 2 µl (400 U) T7 RNA polymerase. This mixture was then added to each tube. The reactions were then incubated at 42° C. for two hours.

The amount of amplified RNA generated was then measured using an acridinium ester-labeled DNA probe directed to the target sequence as described in Arnold et al., PCT WO89/02476 and Arnold et al., *Clin. Chem.* 35:1588–1594 (1989) the former of which enjoys common ownership with the present invention, and both of which are incorporated by reference herein. All reactions were run in quadruplicate except for the negative control, which was run in duplicate. The results shown in Table 9 below indicate that saturating levels of the amplified target sequence are obtained with as little as 2.5 fg of input template RNA at the beginning of the experiment.

TABLE 9

Sensitivity of Enzyme Preparation in an Amplification Reaction

| Amount of Template RNA Added (fg) | Signal (RLU) |
|---|---|
| 250 | 2841164 |
|  | 2802308 |
|  | 2828732 |
|  | 2828837 |
| 25 | 2801357 |
|  | 2968585 |
|  | 2748909 |
|  | 2723562 |
| 2.5 | 2761901 |
|  | 2809799 |
|  | 2932942 |
|  | 2906826 |
| 0 | 2246 |
|  | 2443 |

EXAMPLE 9

Synthesis of cDNA Using Purified Recombinant MMLV-RT from *E. coli* 1200/pUC18N SD9D MMLV Gly Tet(−)

The ability of the recombinant purified MMLV-RT to synthesize cDNA was compared to that of a commercially available reverse transcriptase preparation (U.S. Biochemicals) in an RNA sequencing reaction.

TTE buffer was prepared by mixing 20 ml 1 M Tris-HCl (pH 7.5), 0.4 mM EDTA (pH 8.0) and 281.7 µl triethylamine. Primers had the following sequences:

5'-TACCTTGTTACGACTTCACCCCA-3'    SEQ ID NO:8

5'-CTTAGATGCTTTCAGC-3'    SEQ ID NO:9

The primer were labeled with $^{32}$P at their 5' ends using polynucleotide kinase; procedures for end-labelling nucleic acids are generally known in the art. After being end labelled, the primers were purified by chromatography on Nensorb columns (New England Nuclear) according to the manufacturer's specifications, followed by ethanol precipitation.

Reactions were carried out using either purified recombinant MMLV-RT from *E. coli* 1200/pUC18N SD9D MMLV Gly Tet(−) or reverse transcriptase purchased from a commercial vendor.

Reaction mixtures contained the following reagents in 100 µl final volume: Ten microliters of GPE Buffer (500 mM Tris-HCl (pH 7.6), 175 mM MgCl$_2$, 250 mM KCl, 20 mM spermidine), 8 µof stock rNTPs (25 mM rCTP and rUTP; 65 mM rATP and rGTP), 4 µl of stock dXTPs (10 mM), 0.5 µl 1 M DTT, 20 pmoles $^{32}$P-labelled primer, 20 pmole unlabelled primer, 20 pmoles purified *E. coli* rRNA, 600 U reverse transcriptase. Reactions were established by mixing all components without the reverse transcriptase, then heating the mixture at 95° C. for 5 minutes to denature the template RNA secondary structure. Reactions were then placed at 60° C. for 30 minutes to allow the primers to anneal to the rRNA target. The reaction mixture was cooled to room temperature, and the reverse transcriptase was added. DNA synthesis was carried out at 42° C. for 60 minutes. Reactions were analyzed on 7% polyacrylamide gels essentially as described in Williams et al., *BioTechniques* 4:138–147 (1986).

Both enzymes were found to synthesize cDNA from the RNA template with equal efficiency as judged from the gel electrophoretograms.

EXAMPLE 10

Reverse Transcriptase-Mediated PCR Using Recombinant MMLV-RT from *E. coli* 1200/ pUC18N SD9D MMLV Gly Tet(−)

All PCR reactions were run in a Perkin Elmer-Cetus Model 9600 DNA thermal cycler. The thermal cycler was programmed to incubate the reaction in the following manner and sequence:

94° C. for 3 minutes;

35 cycles between 51° C. for 30 seconds, 72° C. for 2 minutes, and 94° C. for 1 minute;

72° C. for 5 minutes;

4° C. overnight.

Two separate preparations of MMLV-RT were used for this experiment, as well as a lot from the same commercial vendor as above. Different amounts of RT were tested, but 50 U of the enzyme was found to be optimum for all enzyme preparations used. The reagents used in the experiment were as follows: 5×RT Buffer (50 mM Tris HCl (pH 8.3), 75 mM KCl, 3 mM MgCl$_2$, 5 mM DTT); 10×PCR Buffer (Perkin Elmer)(100 mM Tris-HCl (pH 8.3), 500 mM KCl, 15 mM MgCl$_2$, 0.1% gelatin); RT Premix (for each reaction) (4 μl 5×RT Buffer, 0.8 μl of a 25 mM solution of each dNTP, 50 units RT, 100 moles (−) sense primer, water in a total volume of 20 μl); PCR Premix (for each reaction) (8 μl 10×PCR Buffer, 100 pmoles (+) sense primer, 2.5 units Taq DNA Polymerase, and water to a total volume of 80 μl. Probes were stored in 10 mM lithium succinate buffer (pH 5.0), 0.1% lithium lauryl sulfate (LLS).

The probes and primers used for this experiment were designed to be complementary to sequences of the human papilloma virus (HPV) genome. The probes were labeled with acridinium ester as disclosed in Arnold and Nelson, PCT Patent Application No. WO89/02476, hereby incorporated by reference herein.

Crude preparations of unspliced template RNA were made by suspending SiHa cells (which contain HPV nucleic acid sequences integrated into their genome) at a concentration of 1.6×10$^7$ cells/ml in 10 mM sodium phosphate (pH 7.6), 100 mM NaCl. The cells were heated for 15 minutes at 95° C., cooled to room temperature, then diluted into water to the desired concentration. RNA transcripts from the E6 gene were prepared by in vitro transcription of DNA from a plasmid containing the HPV16 E6 gene. This plasmid was constructed by cloning a DNA fragment from the HPV clone described by Matsukura et al., *J. Virol.* 58:979–982 (1986) into pBluescript™ II SK (+) and (−) sense cloning vectors. (Stratagene, San Diego, Calif.) These references are incorporated by reference herein. RNA transcripts were prepared as indicated by the manufacturer.

The amplification reactions were conducted as follows. Target nucleic acids were added to the MMLV-RT premix. This mixture was heated at 95° C. for 2 minutes. The primers were added and allowed to anneal to the target nucleic acids for 10 minutes at 60° C. The reaction mixture was then cooled on ice. Reverse transcriptase was added, and the reaction was incubated at 37° C. for 30 minutes. The reaction was then heated at 95° C. for 10 minutes to inactivate the reverse transcriptase. The mixture was cooled in ice, and two drops of mineral oil were layered onto the surface of each tube.

Taq DNA polymerase, was diluted into the PCR Premix at the concentration indicated above. Eighty microliters of the PCR Premix was then added to each sample. The samples were placed in the thermal cycler at 95° C., and cycling was performed as described above.

Hybridization and detection were carried out as described in Arnold and Nelson, supra. For each hybridization assay, 30 μl of water was given 10 μl of a PCR reaction mixture. The DNA was denatured at 95° C. for 5 minutes. Ten microliters of diluted probe was added and mixed. The tubes were then incubated at 60° C. for 15 minutes. Three hundred microliters of selection reagent was added, the tubes were mixed and incubated at 60° C. for 5 minutes. The tubes were then cooled in ice, and the remaining acridinium ester label was measured in a LEADER luminometer (Gen-Probe Incorporated, San Diego, Calif.).

The results are shown in Table 10.

TABLE 10

| Copies of Template RNA | RNA Type | Origin of Reverse Transcriptase | Average Net RLU |
|---|---|---|---|
| 1 × 10$^7$ | SiHa cell lysate | commercial | 423,084 |
| 1 × 10$^7$ | SiHa cell lysate | E. coli 1200/pUC18N SD9D MMLV Gly Tet (−) | 445,003 |
| 1 × 10$^7$ | E6 transcript | commercial | 2,741,628 |
| 1 × 10$^7$ | E6 transcript | E. coli 1200/pUC18N SD9D MMLV Gly Tet (−) | 2,291,786 |
| 1 × 10$^4$ | E6 transcript | commercial | 103,501 |
| 1 × 10$^4$ | E6 transcript | E. coli 1200/pUC18N SD9D MMLV Gly Tet (−) | 1,395,572 |
| 1 × 10$^5$ | E6 transcript | commercial | 1,317,386 |
| 1 × 10$^5$ | E6 transcript | E. coli 1200/pUC18N SD9D MMLV Gly Tet (−) | 2,283,979 |
| 1 × 10$^6$ | E6 transcript | commercial | 1,661,390 |
| 1 × 10$^6$ | E6 transcript | E. coli 1200/pUC18N SD9D MMLV Gly Tet (−) | 2,951,045 |
| 1 × 10$^7$ | E6 transcript | commercial | 2,294,856 |
| 1 × 10$^7$ | E6 transcript | E. coli 1200/pUC18N SD9D MMLV Gly Tet (−) | 2,421,754 |

What is claimed is:

1. A composition comprising an *Escherichia coli* host cell containing a recombinant expression vector, wherein said recombinant expression vector comprises a gene derived from a Moloney murine leukemia virus (MMLV) sequence, said gene encoding an enzyme comprising a DNA-dependent DNA polymerase activity and an RNA-dependent DNA polymerase activity, wherein said gene expresses said enzyme within said host cell, and wherein said host cell has about 0.1% or less of wild type RNase I activity.

2. A composition comprising an *Escherichia coli* cell having about 0.1% or less of wild type RNase I activity containing:
    i) a recombinant expression vector which comprises a gene encoding a mature native-length Moloney murine leukemia virus (MMLV) reverse transcriptase, and
    ii) reverse transcriptase enzyme expressed by said recombinant expression vector.

3. A composition comprising:
    an *Escherichia coli* host cell that has about 0.1% or less of wild type RNase I activity;
    a recombinant expression vector contained within said host cell, wherein said vector comprises a gene derived from a Moloney murine leukemia virus (MMLV) sequence, said gene encoding an enzyme, said enzyme comprising
        a DNA-dependent DNA polymerase activity,
        an RNA-dependent DNA polymerase activity, and
        an RNAse H activity,
and wherein said vector expresses said gene encoding said enzyme within said host cell.

4. The composition of claim 3 wherein said vector further comprises a ribosome binding site located 5' to said gene and an initiation codon located at the 5' boundary of said gene's coding region.

5. The composition of claim 4 wherein said vector further comprises a nucleotide base sequence consisting of the sequence RRTTTRR located 5' to said gene's coding region.

6. The composition of claim 4 wherein from 7 to 9 nucleotide bases separate said ribosome binding site and said initiation codon.

7. The composition of claim 6 wherein 9 nucleotide bases consisting of the sequence TTAAAAACC separate said ribosome binding site and said initiation codon.

8. The composition of claim 4 wherein said initiation codon is wholly or partly contained within a restriction endonuclease recognition sequence.

9. The composition of claim 8 wherein said restriction endonuclease recognition sequence is recognized by restriction endonuclease Nco I.

10. The composition of claim 6 wherein the gene encoding said enzyme includes the sequence consisting of CTGAACATC coding for amino acids 2 to 4 of said enzyme from the enzyme's amino terminus.

11. The composition of claim 8 wherein the gene encoding said enzyme includes the sequence consisting of CTGAACATC coding for amino acids 2 to 4 of said enzyme from the enzyme's amino terminus.

12. The composition of claim 1 wherein said enzyme encoded by said gene further comprises an RNAse H activity.

13. The composition of claim 2 wherein said reverse transcriptase enzyme comprises an RNAse H activity.

14. The composition of claim 1 wherein said enzyme encoded by said gene consists of the same number of amino acids as mature native viral Moloney murine leukemia virus (MMLV) reverse transcriptase.

15. The composition of claim 1 wherein said host cell is *Escherichia coli* strain 1200, strain MRE 600, strain Q 13 or strain A 19.

16. The composition of claim 15 wherein said host cell is *Escherichia coli* strain 1200.

17. The composition of claim 3 wherein said host cell is *Escherichia coli* strain 1200, strain MRE 600, strain Q 13 or strain A 19.

18. The composition of claim 17 wherein said host cell is *Escherichia coli* strain 1200.

19. The composition of claim 11 wherein said host cell is *Escherichia coli* strain 1200, strain MRE 600, strain Q 13 or strain A 19.

20. The composition of claim 19 wherein said host cell is *Escherichia coli* strain 1200.

21. The composition of claim 2 wherein said cell is *Escherichia coli* strain 1200, strain MRE 600, strain Q 13 or strain A 19.

22. The composition of claim 21 wherein said cell is *Escherichia coli* strain 1200.

* * * * *